United States Patent
Petot et al.

(10) Patent No.: US 7,319,325 B2
(45) Date of Patent: Jan. 15, 2008

(54) TABLE POSITION SENSING FOR MAGNETIC RESONANCE IMAGING

(75) Inventors: Bradford W. Petot, Cleveland, OH (US); Gordon D. DeMeester, Wickliffe, OH (US); William H. Amor, Chagrin Falls, OH (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 10/560,695

(22) PCT Filed: Jun. 1, 2004

(86) PCT No.: PCT/IB2004/001955

§ 371 (c)(1),
(2), (4) Date: Dec. 14, 2005

(87) PCT Pub. No.: WO2005/001497

PCT Pub. Date: Jan. 6, 2005

(65) Prior Publication Data

US 2006/0142655 A1  Jun. 29, 2006

Related U.S. Application Data

(60) Provisional application No. 60/484,003, filed on Jun. 30, 2003.

(51) Int. Cl.
*G01V 3/00* (2006.01)

(52) U.S. Cl. .................................. 324/318; 324/309
(58) Field of Classification Search ........ 324/300–322; 600/407–455
See application file for complete search history.

(56) References Cited

U.S. PATENT DOCUMENTS

| | | | | |
|---|---|---|---|---|
| 4,972,852 A | * | 11/1990 | Koob et al. | 600/415 |
| 5,467,002 A | * | 11/1995 | Brooks | 318/553 |
| 5,551,430 A | * | 9/1996 | Blakeley et al. | 600/410 |
| 5,825,843 A | * | 10/1998 | Kobayashi | 378/20 |
| 6,023,799 A | * | 2/2000 | Wirth et al. | 5/601 |
| 6,045,262 A | * | 4/2000 | Igeta et al. | 378/209 |
| 6,122,538 A | * | 9/2000 | Sliwa et al. | 600/407 |
| 6,661,240 B1 | * | 12/2003 | Johnson et al. | 324/662 |
| 6,822,447 B1 | * | 11/2004 | Yamagata | 324/318 |
| 6,946,836 B2 | * | 9/2005 | Kuhara | 324/307 |
| 7,034,535 B2 | * | 4/2006 | Yamagata | 324/318 |
| 2003/0000355 A1 | | 1/2003 | Butler et al. | 83/13 |

FOREIGN PATENT DOCUMENTS

| | | |
|---|---|---|
| DE | 199 05 239 A1 | 8/2000 |
| JP | 2001-078979 | 3/2001 |
| WO | WO 02/18967 A1 | 3/2002 |

* cited by examiner

Primary Examiner—Brij Shrivastav

(57) ABSTRACT

An MRI apparatus is provided. The MRI apparatus includes a main magnet (12) for generating a main magnetic field in an examination region, a plurality of gradient magnets (16) for generating magnetic field gradients in the main magnetic field, a radio frequency coil (22) for transmitting radio frequency signals into the examination region and exciting magnetic resonance in a subject disposed therein, and a radio frequency coil for receiving the magnetic resonance signals from the subject. The MRI apparatus also includes subject support (52) for supporting the subject, a position controller (60) for controlling the position of the subject support within the examination region, and a position encoder (53) for directly measuring the position of the subject support.

16 Claims, 3 Drawing Sheets

TABLE POSITION SENSING FOR MAGNETIC RESONANCE IMAGING

CROSS REFERENCE TO RELATED APPLICATIONS

This application claims the benefit of U.S. provisional application Ser. No. 60/484,003 filed Jun. 30, 2003, which is incorporated herein by reference.

The following relates to the diagnostic imaging arts. It particularly relates to sensing the position of subject table or other movable subject support used in a magnetic resonance imaging (MRI) apparatus. It is to be appreciated, however, that the present invention will also find application in other types of diagnostic imaging scanners.

Typically, MRI systems require a position, or motion, control system by which a subject is transported on a subject support into, and positioned within, the imaging volume. Current MRI systems employ a support or table for the subject. This support travels horizontally through the magnet, and is driven by a motorized positioning system. In a cylindrical magnet the vertical position of the table-top, and accordingly the subject, is normally constant and the position of the table is adjusted horizontally (i.e. axially) with respect to the bore of the magnet. In vertical field systems the table/subject is often positioned both vertically and horizontally.

Due to a desire to control the position of the subject, some MRI systems incorporate motion control systems having closed-loop control with feedback devices that are attached to a component other than the table-top. Often this is a rotary encoder attached to a motor shaft, drive pinion, or pulley that controls and infers the position of the table. Other motion systems use stepper motors, and open-loop control methods. These motion control systems are generally adequate for simple subject positioning and fulfill the needs for systems with fixed couches and simple RF coils for producing MRI images.

For more complex imaging applications, such as SENSE imaging or applications during which the subject is moved incrementally or continuously, mechanical and control system errors tend to contribute to low levels of position accuracy and repeatability when producing MRI images. These mechanical system errors can be due to belt stretch, gear clearances, part wear, mechanical connections, and other factors that make position accuracy difficult to achieve.

The present invention contemplates an improved apparatus and method that overcomes the aforementioned limitations and others.

In accordance with one aspect of an embodiment of the invention, an MRI apparatus is provided. The MRI apparatus includes a main magnet for generating a main magnetic field in an examination region, a plurality of gradient magnets for generating magnetic field gradients in the main magnetic field, a radio frequency coil for transmitting radio frequency signals into the examination region and exciting magnetic resonance in a subject disposed therein, a radio frequency coil for receiving the magnetic resonance signals from the subject, and a subject support for supporting the subject. The MRI apparatus also includes a position controller for controlling the position of the subject support within the examination region, and a position sensor for directly measuring the position of the subject support.

In accordance with a more limited aspect of the invention, the position sensor includes a plurality of graduated scales disposed on at least one of the subject support and a fixed portion with respect to the MRI apparatus and a plurality of read heads disposed on at least one of the subject support and a fixed portion with respect to the MRI apparatus and opposite the graduated scales for reading the graduated scales.

In accordance with a more limited aspect of the invention, the position sensor detects an absolute position of the subject support.

In accordance with a more limited aspect of the invention, the position of the subject support detected by the position sensor is used by the position controller for controlling the position of the subject support.

In accordance with a more limited aspect of the invention, the position sensor includes a conductive strip disposed on at least one of the subject support and a fixed portion of the MRI apparatus, the conductive strip having a length and a variable resistance along the length of the strip and a contact element disposed on at least one of the subject support and the fixed portion of the MRI apparatus and opposite from the conductive strip, the contact element for making electrical contact with the conductive strip, thereby forming an electrical circuit having an associated current indicative of the position of the subject support.

In accordance with a more limited aspect of the invention, the position sensor includes a target disposed on the subject support and a laser source disposed in a fixed position relative to the MRI apparatus, the laser source for directing a laser beam at the target and detecting signals reflected thereby to provide an indication of the position of the subject support.

In accordance with another aspect of an embodiment of the invention, an MRI apparatus is provided which includes main field means for generating a main magnetic field in an examination region, gradient means for generating magnetic field gradients in the main magnetic field, radio frequency transmit means for transmitting radio frequency signals into the examination region and exciting magnetic resonance in a subject disposed therein, radio frequency receive means for receiving magnetic resonance signals from the subject, subject support means for supporting the subject, position control means for controlling the position of the subject support within the examination region, and position sensing means for directly measuring the position of the subject support.

In accordance with a more limited aspect of the invention, the position sensing means measures an absolute position of the subject support with respect to a fixed reference frame.

In accordance with another aspect of an embodiment of the invention, an MRI method is provided including the steps of generating a main magnetic field in an examination region, generating magnetic field gradients in the main magnetic field, transmitting radio frequency signals into the examination region for exciting magnetic resonance in a subject disposed therein, receiving magnetic resonance signals from the subject, controlling the position of a subject support within the examination region, and directly measuring the position of the subject support.

One advantage of an embodiment of the invention is that it facilitates table/subject position accuracy in the MRI system.

Another advantage of an embodiment of the invention is that it provides a feedback device to directly report the subject support position to the position control system.

Another advantage of an embodiment of the invention is that addresses mechanical and electrical hysteresis errors within an MRI support motion control system.

Numerous additional advantages and benefits will become apparent to those of ordinary skill in the art upon reading the following detailed description of the preferred embodiments.

The invention may take form in various components and arrangements of components, and in various process operations and arrangements of process operations.

The drawings are only for the purpose of illustrating preferred embodiments and are not to be construed as limiting the invention.

Figure 1:
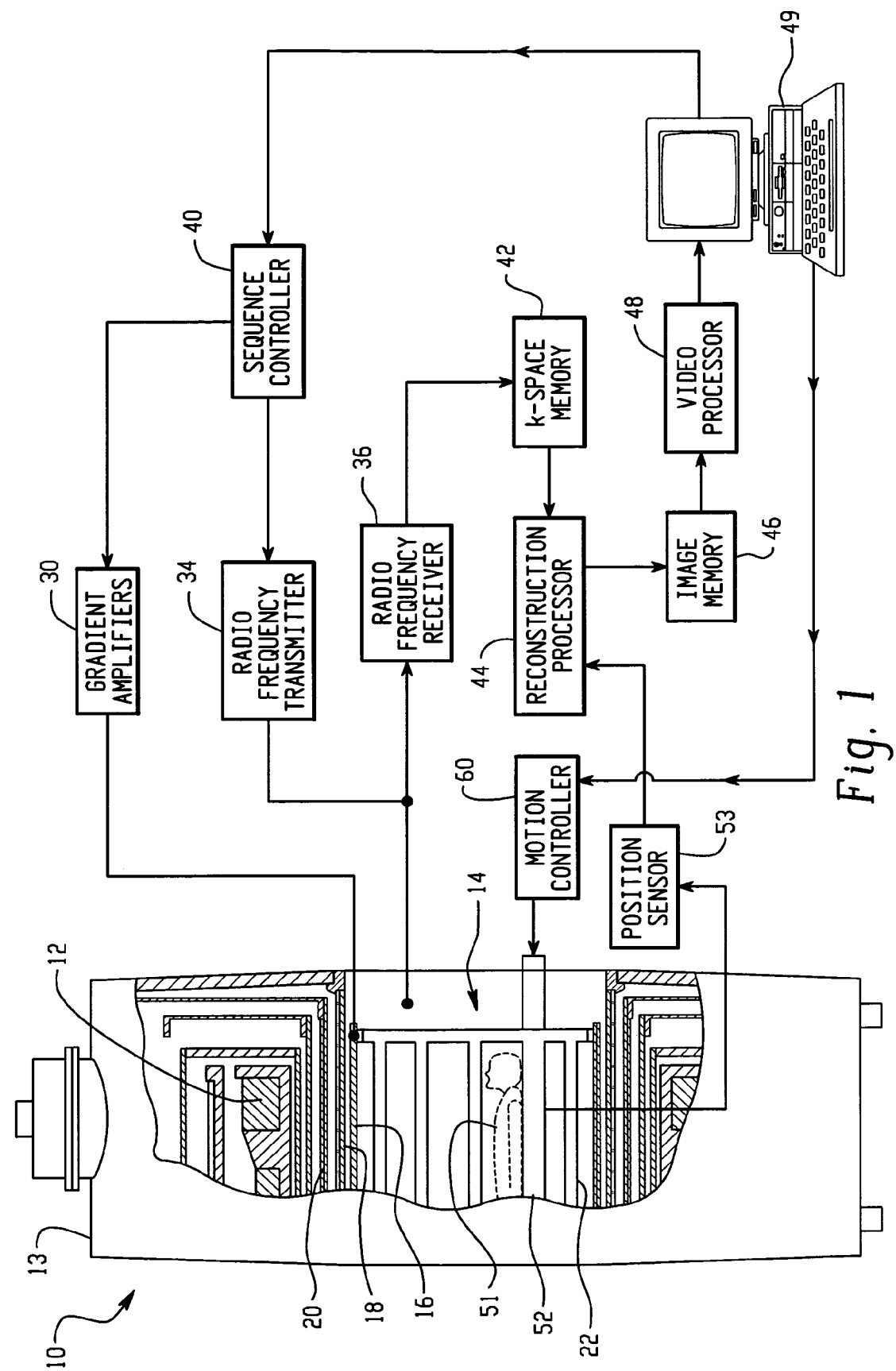
FIG. 1 shows a side view of a magnetic resonance imaging apparatus with a movable subject support and a position sensor for directly measuring the position of the support.

With reference to FIG. 1, an MRI apparatus 10 includes a cylindrical main magnet 12, which is preferably superconducting and cryoshielded. The main magnet 12, and the housing 13 in which it is disposed, defines a magnet bore 14, or examination region, inside of which a subject 51 is placed for imaging. The main magnet 12 produces a spatially and temporally constant and uniform main magnetic field oriented along a longitudinal (z) axis of the bore 14. Instead of a superconducting magnet, a non-superconducting magnet can be used. Moreover, a vertical magnet, an open magnet; or other type of main magnet can be employed instead of the illustrated horizontal cylindrical main magnet 12.

The MRI apparatus also includes magnetic field gradient coils including a primary gradient coil 16 and optionally a shield gradient coil 18 that cooperatively produce magnetic field gradients in the bore 14 for spatially encoding magnetic resonance signals, for producing magnetization-spoiling field gradients, or the like. Preferably, the magnetic field gradient coils include coils configured to produce magnetic field gradients in three orthogonal directions including transverse x- and y-directions. In addition to the shield coil 18, an optional cold shield 20 provides a high conductivity eddy current surface for residual gradient fields thus protecting the magnet coils still further away.

A radio frequency coil assembly 22, for example a whole body coil, generates radio frequency pulses for exciting magnetic resonances. The radio frequency coil assembly 22 can also serve to detect magnetic resonance signals. Optionally, additional local radio frequency coils or phased radio frequency coil arrays (not shown) are included for exciting and/or detecting magnetic resonances at localized areas in the bore 14.

Gradient pulse amplifiers 30 deliver controlled electrical currents to the magnetic field gradient coils 16, 18 to produce selected magnetic field gradients. A radio frequency transmitter 34, preferably digital, applies radio frequency pulses or pulse packets to the radio frequency coil assembly 22 to generate selected magnetic resonance excitations. A radio frequency receiver 36 also coupled to the radio frequency coil assembly 22 receives magnetic resonance signals. If more than one radio frequency coil is provided (such as a local coil or phased coil array), then different coils are optionally used for the magnetic resonance excitation and detection operations.

A sequence controller 40 communicates with the gradient amplifiers 30 and the radio frequency transmitter 34 to produce selected transient or steady state magnetic resonance configurations in the subject, to spatially encode such magnetic resonances, to selectively spoil magnetic resonances, or otherwise generate selected magnetic resonance signals characteristic of the subject. The generated magnetic resonance signals are detected by the radio frequency receiver 36, and stored in a k-space memory 42. The imaging data is reconstructed by the reconstruction processor 44 to produce an image representation that is stored in an image memory 46. In one embodiment the reconstruction processor 44 performs an inverse Fourier transform reconstruction.

The resultant image representation is processed by a video processor 48 and can then be displayed on a user interface 49, which can be a personal computer, workstation, or other type of computer and can be stored thereon. The user interface 49 also allows an operator to communicate with the magnetic resonance sequence controller 40 and position controller 60 to select magnetic resonance imaging sequences, modify imaging sequences, execute imaging sequences, and protocols and so forth. Alternately, the sequence controller communicates with the position controller to coordinate motion of the subject support with the imaging sequence.

The MRI apparatus also includes a movable subject support 52 for moving a subject within the examination region. In one embodiment, the subject support is a wheeled table or other movable support that is adapted to mechanically dock with the magnetic resonance imaging apparatus. In another embodiment, the subject support is integrated with the MRI system and is movable therein. Regardless of the type of support, the subject support is movable for positioning the subject within the examination region.

The position of the support 52 is controlled by the position controller 60. In one embodiment, the position controller 60 includes a motor drive and linkage to the patient support which controls the position of the patient support as is known by one of ordinary skill in the art. Alternately, a drive pinion, pulley system, stepper motor, or the like controls the position of the table.

As described more fully below, the MRI apparatus also includes a position sensor, or encoder, 53 for directly detecting the position of the subject support with respect to a given reference frame.

Figure 2:
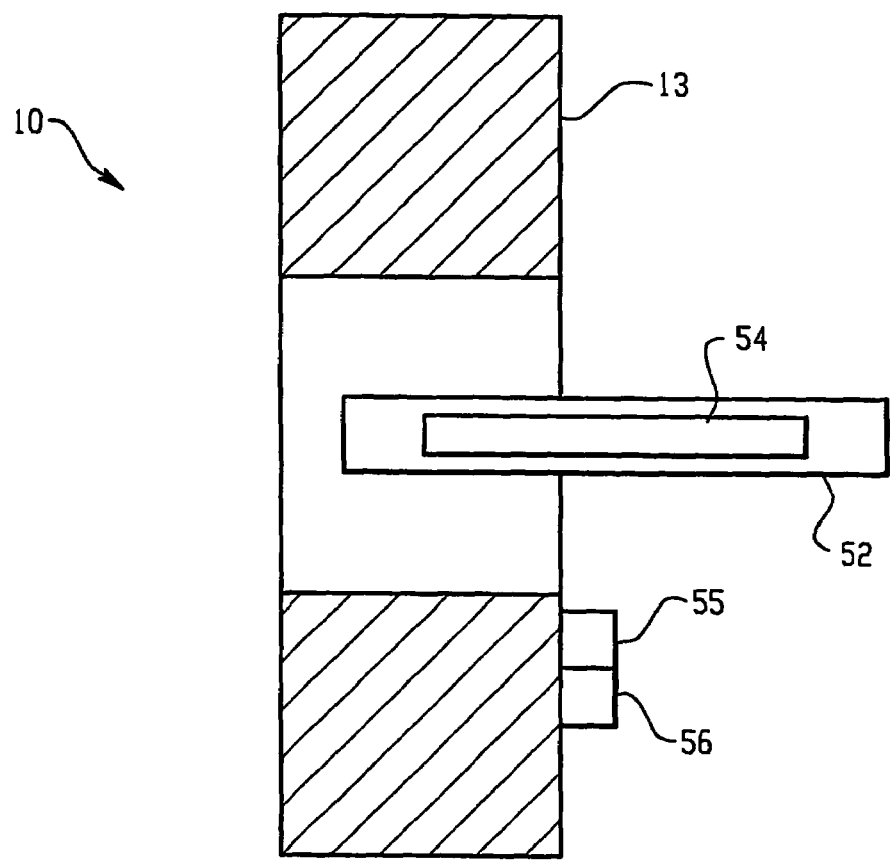
FIG. 2 shows an embodiment of a position sensor.

Turning to FIG. 2, the position sensor 53 is shown in greater detail. In one embodiment, the position sensor includes a graduated scale 54 disposed on the subject support and first (or coarse) and second (or fine) read heads 55, 56 disposed on the MRI housing 13.

Figure 3:
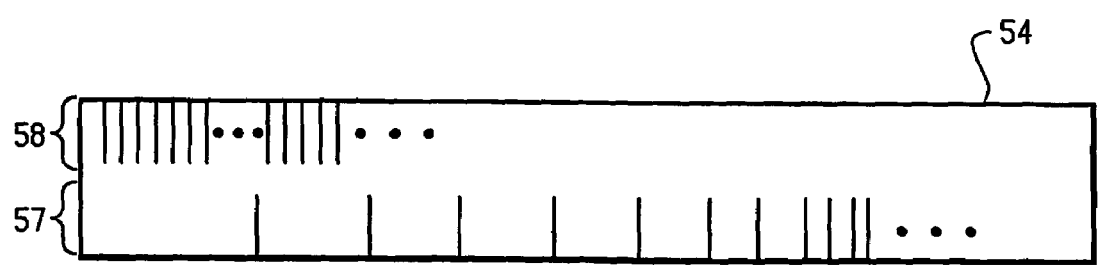
FIG. 3 shows a graduated scale of a position sensor.

The graduated scale includes two sets of gradations, a first (or coarse resolution) set 57 and a second (or fine resolution) set 58, as shown in FIG. 3. As can also be seen in the embodiment shown in FIG. 3, the gradations of each scale are variably spaced in moving from left to right. For example, with respect to the coarse scale, the distance between gradations decreases in going from left to right along the scale. With respect to the fine scale, for each set of gradations between the gradations of the coarse scale, the distance between gradations decreases in going from left to right. By incorporating such variable distances between gradations, the absolute position of the subject support can be monitored.

In one embodiment the graduated scale is made of a strip of polyester film which is attached to the subject support. Glass strips are also contemplated.

The coarse 55 and fine 56 read heads include optical cameras which are directed at the coarse 57 and fine 58 scales respectively. Each read head includes an optical mask for detecting the graduations, or tick-marks, of its respective scale. Accordingly, as the graduated scales move with respect to the read heads, the read heads track the number of tick marks that pass the read heads. Given the distances between the tick-marks for the coarse and fine scales, the absolute position of the subject support can be determined from the signals of the read heads.

It is to be understood that the read heads could be disposed on the subject support and the scales could be disposed on the MRI housing and that the position of the subject support could be directly determined as described above.

In another embodiment, only one set of gradations and one read head is used.

Figure 4:
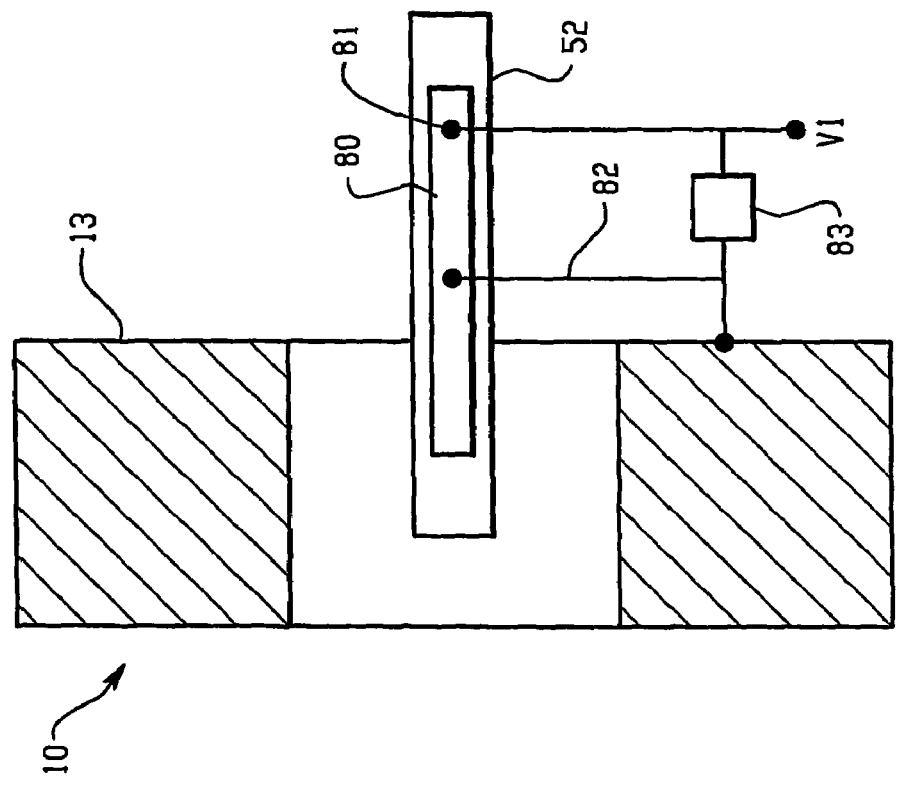
FIG. 4 shows an embodiment of a position sensor using a resistive encoder.

In an alternate embodiment as shown in FIG. 4, a resistive position encoder is utilized. In this embodiment, a conductive strip 80 with variable resistance along the length of the strip is placed on the subject support. A voltage V1 is applied at, for example, one end 81 of the conductive strip. A contact element 82 is disposed on the MRI housing and makes electrical contact with the conductive strip, thereby forming an electrical circuit having an associated current which is measured by an ampmeter 83. Accordingly, as the subject support is moved, the measured current provides an indication of the position of the subject support. Alternately, a current is applied to the circuit and voltage is measured as the subject support is moved.

Figure 5:
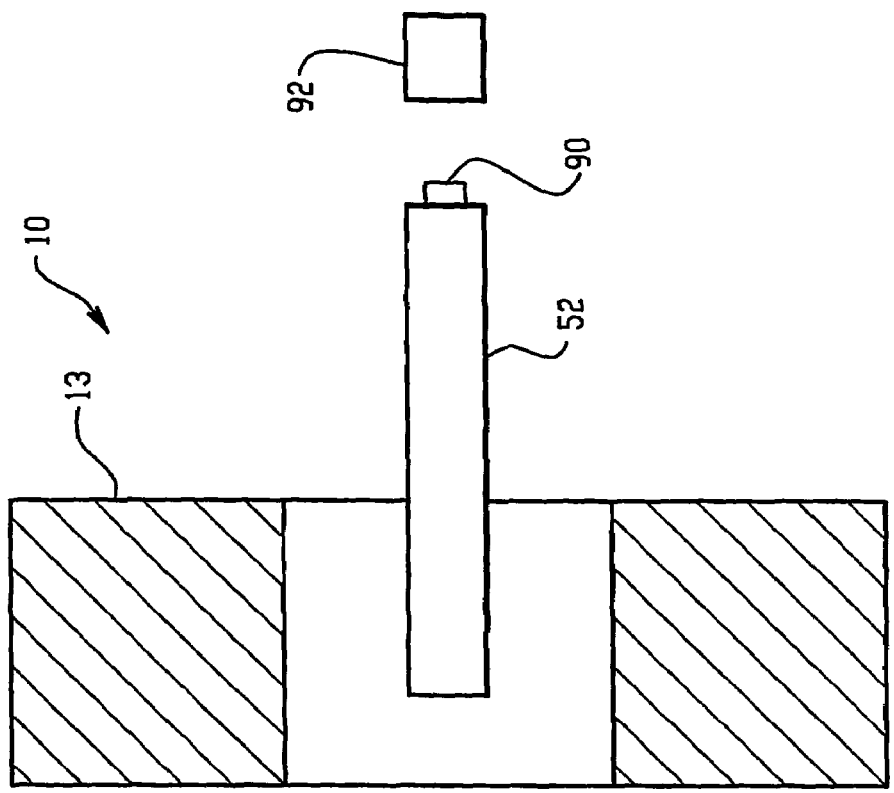
FIG. 5 shows an embodiment of a position sensor using a laser-based encoder.

In another embodiment as shown in FIG. 5, a laser based position encoder is utilized. In this embodiment, a target 90 is placed on the subject support and a laser source 92 is aimed at the target. The laser directs a signal at the target which is reflected back to the laser and is detected thereby. The time of travel of the signal from the laser to the target and back to the laser provides an indication of the position of the subject support. In an alternate embodiment, the laser is directed at the subject support itself, rather than at a placed target.

It is to be understood that rather than the linear transducers described above, rotary transducers are also contemplated.

In operation, a region of interest for imaging the subject and the parameters of the imaging protocol are selected. The subject is placed on the subject support 52 and the region of interest is moved into the examination region 14, preferably into the isocenter of the main magnetic field. The movement of the subject support is controlled by the position controller 60 and the position sensor 53 directly measures the position of the support 52 with respect to the given reference frame, for example a reference frame attached to the MRI housing.

In one embodiment, the position of the subject support is fed from the position sensor 53 to the motion controller 60 to directly control the movement of the support generated by the motion controller.

In another embodiment, the output of the position sensor 53 is compared to the target position of the motion controller 60 and an error between the two values is determined. This position error information is then used by the motion controller to correct for the error.

In yet another embodiment, the position information from the position encoder 53 is fed to the reconstruction processor for use in reconstructing images resulting from stationary and/or moving table imaging protocols. Here, position data is coordinated with the MRI image data to allow for precise measurement of image features.

The invention has been described with reference to the preferred embodiments. Obviously, modifications and alterations will occur to others upon reading and understanding the preceding detailed description. It is intended that the invention be construed as including all such modifications and alterations insofar as they come within the scope of the appended claims or the equivalents thereof

What is claimed is:

1. An MRI apparatus comprising:
    a main magnet for generating a main magnetic field in an examination region;
    a plurality of gradient magnets for generating magnetic field gradients in the main magnetic field;
    a radio frequency coil for transmitting radio frequency signals into the examination region and exciting magnetic resonance in a subject disposed therein;
    a radio frequency coil for receiving the magnetic resonance signals from the subject;
    a subject support for supporting the subject;
    a position controller for controlling the position of the subject support within the examination region; and
    a position sensor for directly measuring the position of the subject support.

2. An MRI apparatus as set forth in claim 1 wherein the position sensor comprises a plurality of graduated scales disposed on at least one of the subject support and a fixed portion with respect to the MRI apparatus and a plurality of read heads disposed on at least one of the subject support and a fixed portion with respect to the MRI apparatus and opposite the graduated scales for reading the graduated scales.

3. An MRI apparatus as set forth in claim 1 wherein the position sensor detects an absolute position of the subject support.

4. An MRI apparatus as set forth in claim 1 wherein the position of the subject support detected by the position sensor is used by the position controller for controlling the position of the subject support.

5. An MRI apparatus as set forth in claim 1 wherein the position sensor comprises:
    a conductive strip disposed on at least one of the subject support and a fixed portion of the MRI apparatus, the conductive strip having a length and a variable resistance along the length of the strip; and
    a contact element disposed on at least one of the subject support and the fixed portion of the MRI apparatus and opposite from the conductive strip, the contact element for making electrical contact with the conductive strip, thereby forming an electrical circuit having an associated current indicative of the position of the subject support.

6. An MRI apparatus as set forth in claim 1 wherein the position sensor comprises:
    a target disposed on the subject support; and
    a laser source disposed in a fixed position relative to the MRI apparatus, the laser source for directing a laser beam at the target and detecting signals reflected thereby to provide an indication of the position of the subject support.

7. An MRI apparatus comprising:
    main field means for generating a main magnetic field in an examination region;
    gradient means for generating magnetic field gradients in the main magnetic field;
    radio frequency transmit means for transmitting radio frequency signals into the examination region and exciting magnetic resonance in a subject disposed therein;
    radio frequency receive means for receiving magnetic resonance signals from the subject;

subject support means for supporting the subject;
position control means for controlling the position of the subject support within the examination region; and
position sensing means for directly measuring the position of the subject support.

8. An MRI apparatus as set forth in claim 7 wherein the position sensing means measures an absolute position of the subject support with respect to a fixed reference frame.

9. An MRI apparatus as set forth in claim 7 wherein the position sensing means comprises a plurality of graduated scales disposed on at least one of the subject support and a fixed portion with respect to the MRI apparatus and a plurality of read heads disposed on at least one of the subject support and a fixed portion with respect to the MRI apparatus and opposite the graduated scales for reading the graduated scales.

10. An MRI apparatus as set forth in claim 7 wherein the position of the subject support measured by the position sensing means is used by the position control means for controlling the position of the subject support.

11. An MRI apparatus as set forth in claim 7 wherein the position sensing means comprises:
a conductive strip disposed on at least one of the subject support and a fixed portion of the MRI apparatus, the conductive strip having a length and a variable resistance along the length of the strip; and
a contact element disposed on at least one of the subject support and the fixed portion of the MRI apparatus and opposite from the conductive strip, the contact element for making electrical contact with the conductive strip, thereby forming an electrical circuit having an associated current indicative of the position of the subject support.

12. An MRI apparatus as set forth in claim 7 wherein the position sensing means comprises:
a target disposed on the subject support; and
a laser source disposed in a fixed position relative to the MRI apparatus, the laser source for directing a laser beam at the target and detecting signals reflected thereby to provide an indication of the position of the subject support.

13. An MRI method comprising the steps of:
generating a main magnetic field in an examination region;
generating magnetic field gradients in the main magnetic field;
transmitting radio frequency signals into the examination region for exciting magnetic resonance in a subject disposed therein;
receiving magnetic resonance signals from the subject;
controlling the position of a subject support within the examination region; and
directly measuring the position of the subject support.

14. An MRI method as set forth in claim 13 wherein the step of directly measuring the position of the subject support includes measuring an absolute position of the subject support with respect to a fixed reference frame.

15. An MRI method as set forth in claim 13 wherein the step of controlling the position of the subject support includes using the direct measurements of the position of the subject support.

16. A diagnostic imaging apparatus comprising:
an examination region for receiving a subject to be examined;
a subject support for supporting the subject within the examination region;
a position controller for controlling the position of the subject support within the examination region; and
a position sensor for directly measuring the position of the subject support, wherein a first portion of the position sensor is disposed on at least one of: i) the subject support; and ii) a generally fixed location with respect to the diagnostic imaging apparatus; and a second portion of the position sensor is disposed on at least one of: i) the subject support; and ii) a generally fixed location with respect to the diagnostic imaging apparatus and opposite the first portion of the position sensor.

* * * * *